(12) United States Patent
Seifert et al.

(10) Patent No.: US 9,539,033 B2
(45) Date of Patent: Jan. 10, 2017

(54) LATERAL SPINOUS PROCESS SPACER

(71) Applicant: GLOBUS MEDICAL, INC., Audubon, PA (US)

(72) Inventors: Jody L. Seifert, Birdsboro, PA (US); Jamie Carroll, Drexel Hill, PA (US); David C. Paul, Phoenixville, PA (US); Michael L. Boyer, Phoenixville, PA (US); Jason Zappacosta, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 314 days.

(21) Appl. No.: 13/958,185

(22) Filed: Aug. 2, 2013

(65) Prior Publication Data

US 2015/0039032 A1     Feb. 5, 2015

Related U.S. Application Data

(63) Continuation of application No. 12/107,222, filed on Apr. 22, 2008, now Pat. No. 8,523,910.

(51) Int. Cl.
| | |
|---|---|
| *A61B 17/88* | (2006.01) |
| *A61B 17/70* | (2006.01) |
| *A61B 17/02* | (2006.01) |
| *A61F 2/30* | (2006.01) |
| *A61M 29/00* | (2006.01) |
| *A61B 17/56* | (2006.01) |

(52) U.S. Cl.
CPC ......... *A61B 17/7068* (2013.01); *A61B 17/025* (2013.01); *A61B 17/7062* (2013.01); *A61B 90/39* (2016.02); *A61B 2017/0256* (2013.01); *A61B 2017/564* (2013.01); *A61F 2002/3008* (2013.01); *A61F 2250/0098* (2013.01); *A61M 29/00* (2013.01)

(58) Field of Classification Search
CPC  A61F 2/44; A61F 2310/00023; A61F 2/4611; A61F 2002/4475; A61F 2/4405; A61F 2/447
USPC ...................... 606/246–249; 623/17.11–17.16
See application file for complete search history.

(56) References Cited

U.S. PATENT DOCUMENTS

| | | | |
|---|---|---|---|
| 7,101,375 B2 | 9/2006 | Zucherman et al. | |
| 2005/0245937 A1 | 11/2005 | Winslow | |
| 2006/0265066 A1 | 11/2006 | Zucherman et al. | |
| 2006/0293662 A1* | 12/2006 | Boyer, II ........... | A61B 17/1671 606/249 |
| 2007/0032790 A1 | 2/2007 | Aschmann et al. | |
| 2008/0243250 A1* | 10/2008 | Seifert ............... | A61B 17/7062 623/17.16 |

\* cited by examiner

*Primary Examiner* — Mary Hoffman
*Assistant Examiner* — Tara R Carter

(57) ABSTRACT

Interspinous process implants are disclosed. Also disclosed are systems and kits including such implants, methods of inserting such implants, and methods of alleviating pain or discomfort associated with the spinal column.

17 Claims, 15 Drawing Sheets

… …  … …  … …  … …

LATERAL SPINOUS PROCESS SPACER

CROSS-REFERENCE TO RELATED APPLICATIONS

The present application is a continuation application of U.S. patent application Ser. No. 12/107,222 filed on Apr. 22, 2008, which is incorporated by its entirety herein.

FIELD OF THE INVENTION

The present invention is generally directed to intervertebral or interspinous process implants, systems and kits including such implants, methods of inserting such implants, and methods of treating spinal stenosis or for alleviating pain or discomfort associated with the spinal column.

BACKGROUND OF THE INVENTION

Occurrences of spinal stenosis are increasing as society ages. Spinal stenosis is the narrowing of the spinal canal, lateral recess or neural foramen, characterized by a reduction in the available space for the passage of blood vessels and nerves. Clinical symptoms of spinal stenosis include extremity pain, radiculopathy, sensory or motor deficit, bladder or bowel dysfunction, and neurogenic claudication. Pain associated with such stenosis can be relieved by surgical or non-surgical treatments, such as medication, physical therapy, back braces and the like. While spinal stenosis is generally more prevalent of the elderly, it can occur in individuals of all ages and sizes.

There is a need for implants that may be placed between spinal processes for minimally invasive surgical treatment of spinal stenosis.

SUMMARY OF THE INVENTION

Certain embodiments of the present invention are generally directed to minimally invasive implants, in particular, interspinous process implants or spacers. Other embodiments of the invention are further directed to systems and kits including such implants, methods of inserting such implants, and methods of alleviating pain or discomfort associated with the spinal column.

Some embodiments of the present invention provide spacers or implants and methods for relieving pain and other symptoms associated with spinal stenosis, by relieving pressure and restrictions on the blood vessels and nerves. Such alleviation of pressure may be accomplished in the present invention through the use of an implant placed between the spinous process of adjacent vertebra.

BRIEF DESCRIPTION OF THE DRAWINGS

The invention will be more readily understood with reference to the embodiments thereof illustrated in the attached figures, in which.

DETAILED DESCRIPTION OF THE INVENTION

Figure 3:
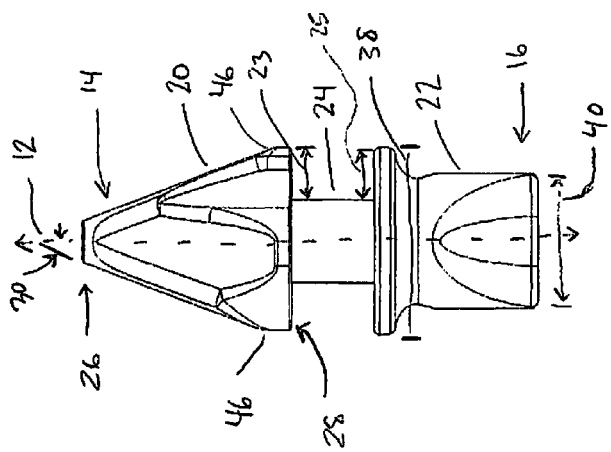
FIG. 3 is top view of the implant of FIG. 1.

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Implants

Some embodiments of the present invention are directed to minimally invasive implants, in particular, interspinous process spacers. Implants in accordance with the invention may come in many shapes and sizes. The illustrative embodiments provided herein-below provide guidance as to the many types of implants that may be advantageously used in accordance with the present invention. In particular, the implants are adapted such that their insertion technique (including methods of the present invention) is minimally invasive, and generally simpler, and/or safer than those installed in open or more invasive techniques. According to one aspect, implants according to the present invention may be advantageously inserted into a patient as an out-patient procedure.

Embodiments of the present invention include implants adapted to be placed between first and second adjacent spinous processes. The implants may be adapted such that after insertion of an implant into a patient, a portion of the implant maintains a desired amount of distraction or spacing between two adjacent spinous processes. The implants or portions thereof that substantially maintain a desired spacing between spinous processes are also referred to herein as "7spacers." In various embodiments described herein, the implants may include spinous process support surfaces, indented portions or saddle portions spaced apart by a distance (a) (FIG. 4), which generally corresponds to a desired distance for distraction or spacing of two adjacent spinous processes. Other embodiments similarly provide a desired distance for distraction or spacing of two adjacent spinous processes. Depending on the material and/or design of the implant, the desired distraction or spacing distance may vary somewhat after insertion, for example if a patient moves its spine into a position that causes further distraction. For example, in certain embodiments the implant may be resiliently compressible or expandable in the cranial-caudal direction such that the implant may support and or adjust to dynamic movement of the spine. Although not depicted in the figures discussed below, it is contemplated that embodiments of the present invention may be extended to provide distraction or spacing of more than two adjacent spinous processes.

Implants according to the present invention may be adapted to be inserted between a first and second spinous process at any region in the spine. Although typically implants according to the present invention may be inserted in the lumbar region, it is contemplated that it is possible to configure inserts according to the present invention for insertion into other regions such as for example, the thoracic or cervical region. In general, implants according to the invention may have varying profiles when viewed in a saggittal or axial plane. In this regard, the implants can have varied cross-sectional shapes to conform to the varied anatomical shapes of the interspinous spaces of the spine.

Certain embodiments of implants of the invention may secure themselves in place without a supplemental attachment mechanism or fastening device attached directly to a spinous process or other portion of the spine. Alternatively, implants in accordance with the invention may be attached to one or more spinous processes or other portion of the spine, or may attach to itself in such a manner as to secure the implant between two adjacent spinal processes. By way of example, implants in accordance with the present invention may be attached to one or both spinous processes or other portion of the spine by one or more pins, screws, wires, cables, straps, surgical rope, sutures, elastic bands, or other fastening devices. Other exemplary implants, attachment mechanisms, and methods are disclosed in U.S. patent application Ser. Nos. 1/366,388 and 11/691,357, the entire contents of which are incorporated herein by reference. "Securing" implants between spinous processes, does not require that the implant not move at all, but rather means that the implant does not move so far away from between the spinous processes that it does not perform the function of maintaining a desired distraction distance or space between the adjacent spinous processes.

Implants in accordance with the present invention may be secured between spinous processes by methods other than using a fastening device. For example, according to certain embodiments, implants in accordance with the present invention may be secured in place with respect to spinous processes by mechanical forces resulting from the design of the implant, including the shape itself. Exemplary implants may also be secured to spinous processes, by surface modifications to portions of the implant, such as to create frictional forces or other bonds between the implant and spinous processes. Such surface modifications may include mechanical modifications to the surface and/or one or more coatings. Exemplary coatings which may be utilized include, but are not limited to, titanium plasma sprays and chrome sprays or the like. Such mechanical forces and/or surface modifications may be utilized in addition to, or in place of various other attachment methods described herein.

Figure 4:
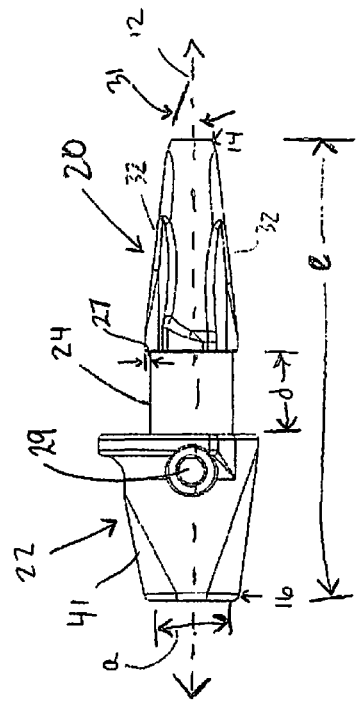
FIG. 4 is side view of the implant of FIG. 1.
Figure 1:
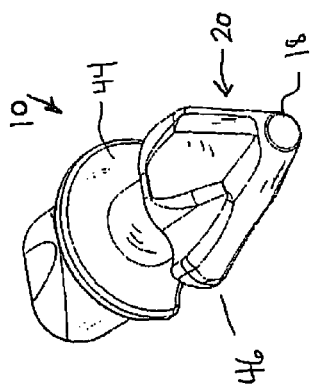
FIG. 1 is a front perspective view of one embodiment of an implant according to the invention for creating, increasing, or maintaining distraction between adjacent spinous processes.

Referring now to FIGS. 1-4, one exemplary embodiment of an implant 10 according to the invention is shown for creating, increasing, or maintaining distraction between adjacent spinous processes. In general, implant 10 is adapted and configured to be placed between adjacent spinous processes. For example, referring to FIGS. 33-34, a posterior and side view, respectively, of implant 10 is shown in implanted positions between to two adjacent spinous processes 5. As best seen in FIGS. 1-4, implant 10 generally comprises an elongate member extending laterally along axis 12 from a first lateral end 14 to a second lateral end 16. In one embodiment, implant 10 may be cannulated with a central cannula or opening 18 extending along axis 12. One skilled in the art may appreciate that, in operation, cannulation 18 may facilitate advancement, travel, or delivery to an implant location over a guidewire. In another variation, implant 10 may be solid and without a cannulation and in this regard may be advanced or inserted by a practitioner without the use of a guidewire. According to one embodiment, implant 10 may comprise a unitary body with a general barbell-like or spade-like shape, and generally includes a first end portion or distraction portion 20 adjacent first end 14, a second end portion or trailing end portion 22 adjacent second end 16 and a central support portion or saddle portion 24 disposed between the distraction and trailing end portions 20, 22. In one embodiment, a radio-opaque marker 29 may extend through a portion of implant 10. As best seen in FIG. 4, support portion 24 may have a height (a) and width (d), and the implant may have an overall length (e). As best seen in FIG. 3, in one embodiment, implant 10 has a generally arrow or spade shaped profile or perimeter when viewed perpendicular to axis 12 and distraction portion 20 is generally flatter or narrower when viewed from the side, as shown in FIG. 4.

Distraction portion 20 is generally configured and dimensioned to facilitate lateral insertion between adjacent spinous processes. In one embodiment, distraction portion 20 generally comprises a frustoconical, wedged, or tapered shape widening along axis 12 from a tip 26 adjacent the first end 14 to a shoulder 28 adjacent central support portion 24. In one exemplary embodiment, the distraction portion 20 resembles a generally flattened spear head that tapers greater in a lateral direction than in vertical direction. In this regard, as best seen in FIG. 3, portion 20 is generally tapered along a cone angle 30 in a lateral direction and cone angle 30 may be between about 10 and 65 degrees. Also, as best seen in FIG. 4, portion 20 is generally ramped or tapered along a cone angle 31 in a vertical direction and cone angle 31 may be between about 1 and 65 degrees. In alternate embodiments, cone angle 30 may be between about 30 and 80 degrees, and cone angle 31 may be between about 5 and 30 degrees.

In one variation, distraction portion 20 may additionally include a ramped, wedged, fluted, grooved, a cam or cam-like profile section 32 intermediate the tip 26 and shoulder 28. In this regard, the ramped section 32 and more gradual taper in the vertical direction facilitates lateral insertion with the generally flatter dimension positioned between the adjacent spinous processes. In one variation, distraction portion 20 is configured and dimensioned such that when implant 10 is advanced between adjacent spinous processes laterally along axis 12, the adjacent spinous processes engage or ride upon ramp section 32 and are distracted or separated apart as implant 10 is advanced laterally along axis 12 during implantation. The rate at which the distraction occurs may be readily controlled by a surgeon by controlling the rate of lateral advancement of implant 10, so that the surgeon may advance implant 10 along axis 12 as slow or as fast as desired. In this regard, implant 10 may be characterized as self-distracting, as the implant itself distracts or separates the spinous processes as it is being implanted, i.e. without requiring an additional distraction step or device.

Trailing end portion 22 adjacent second end 16 may comprise a flange and/or generally frustoconical, wedged, or tapered shape narrowing along axis 12 from a major dimension 38 adjacent central support portion 24 to a minor dimension 40 adjacent the second end 16. Those skilled in the art will appreciate that a tapered feature may be desirable to minimize wear and trauma with adjacent soft tissue and/or bone when implant 10 is installed in a patient. In one embodiment, trailing end portion 22 may comprise a flange portion 39 that extends circumferentially about central support portion 24. In one variation, flange portion 39 may extend around a majority of the circumference of support portion 24, and in one embodiment, best seen in FIG. 4, flange 39 may be generally flatter along the bottom section. In another embodiment trailing end portion 22 may comprise a tapered portion 41 that may be generally symmetrical to distraction portion 20 with generally similar lateral length and cone angle 31. In alternate embodiments, however, the trailing end portion 22 need not be symmetrical whatsoever and may have any shape irrespective of the dimension of distraction portion 20.

Figure 2:
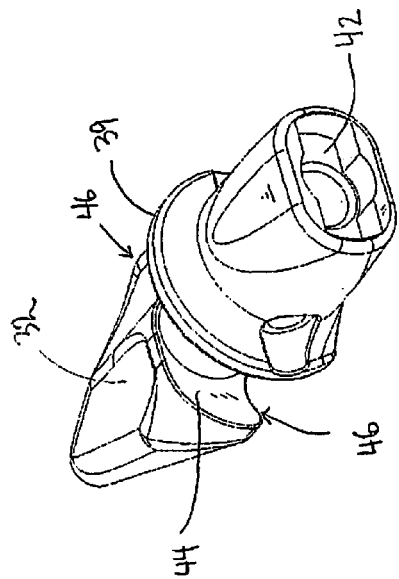
FIG. 2 is a rear perspective view of the implant of FIG. 1.
Figure 5:
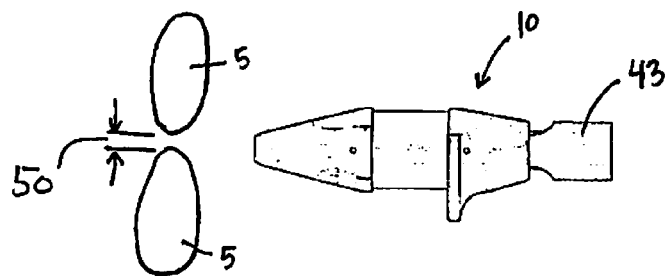
FIGS. 5-9 are views demonstrating various steps according to one embodiment of a method of installation of the implant of FIG. 1.
Figure 6:
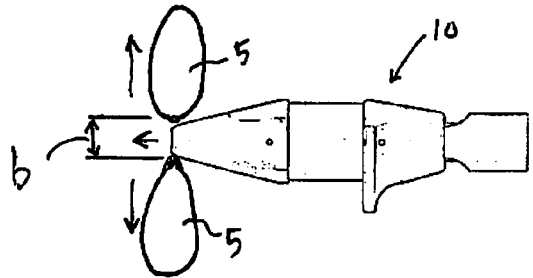
Figure 7:
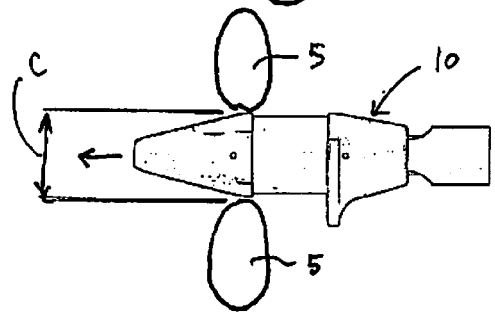
Figure 8:
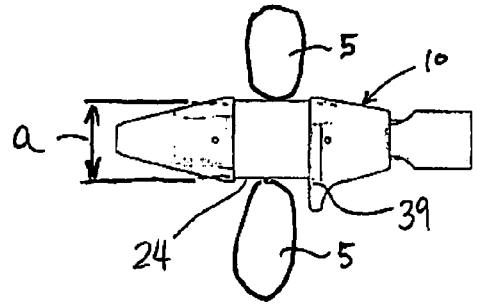

In one embodiment, a socket or indentation 42 may be provided to receive an installation or driving tool with a correspondingly shaped driver tool. Any known driving tools and engagement means may be used, including but not limited to, a flat driver, a star shaped driver, a threaded driver, or a custom shaped driver, among others. In one variation a driver 43 may be provided with an external shape configured to fit within socket 42. In another variation, driver 43 may comprise a flexible shaft such that the implant 10 may travel along a curved or arcuate path. For example, those skilled in the art may appreciate that such a flexible driver configuration may facilitate insertion of an implant in the L5-S1 region of the spine where direct lateral insertion may be more difficult. As best seen in FIG. 2, indent 42 may be concentric with cannula 18 to facilitate insertion with a cannulated driver tool over a guidewire extending through cannula 18 and indentation 42. In one variation, a threaded section may be provided internal to indentation 42 to accommodate a threaded connection of an installation or removal tool (FIG. 26) with implant 10. In this regard, the threaded connection between a tool and the implant facilitates a laterally fixed relative connection between the implant and tool so that the implant does not dislodge from the trailing end and may efficiently transfer both lateral translational and rotational forces applied on the tool to the implant during installation. One skilled in the art may appreciate that the threaded connection may also facilitate the removal of implant 10 from the body of a patient should a surgeon so desire.

Central support portion 24 is provided between the distraction and trailing end portions 20, 22. In one embodiment, support portion 24 may have a diameter or height (a) less than the major dimensions 28, 38 of portions 20, 22. In this regard, when viewed from the top, as seen in FIG. 3, implant 10 may appear to have a general H-like shape or a barbell-like shape, with the lateral sides 20, 22, being longitudinally spaced a distance 23, 25, respectively beyond central support portion 24. In one variation, distances 23, 25 do not need to be equal. According to one embodiment, lateral sides 20, 22 may be spaced a distance 23, 25 between about 1 mm and about 6 mm from the support portion 24. In one particular embodiment, distances 23, 25 is about 4-5 mm.

Referring to FIG. 4, when viewed from the side, the transition from the distraction portion 20 to the central support portion 24 is less abrupt to facilitate lateral insertion into the interspinous space with implant 10 in a first or lower profile position. In one variation, as shown in FIGS. 1-4, a small transition bump 27 or height differential may be provided at the transition from the distraction portion 20 to the central support portion 24. According to one embodiment bump 27 may have a height of about 1 mm. In other embodiments a smooth transition may be provided without a bump or height differential. For example, in one exemplary embodiment, a flexible bumper member or sleeve may be positioned about support portion so as to be flush with distraction portion 20 when viewed from the side. Implant 10 is configured and dimensioned to facilitate rotation of about 90 degrees into a second or higher profile position upon implantation and once distraction portion 20 has passed laterally beyond the spinous processes. As best seen in FIG. 3 when viewed from the top, in one embodiment, the transition from the distraction portion 20 to the central support portion 24 and the transition from the central support portion 24 to trailing end portion 22 may be abrupt. In this regard, a shoulder wall section 44 may be formed at either end of central support portion 24, and when implant 10 is implanted, wall sections 44 may serve to limit or block movement of the implant along axis 12 and/or dislodgement from the interspinous space.

In one embodiment, textures, such as knurling, serrations, abrasions, or other similar features may be provided along the surface of central support portion 24 to facilitate gripping or frictional contact with bone, such as the spinous process, to limit or reduce movement and/or dislodgement from the interspinous space once installed. In one variation, one or more barbs 46 may extend from wall sections 44. Barbs 46 may have a saw-tooth shape, have an angled undercut, or may have other sharpened end portions to grip and/or engage tissue or bone to resist counter rotation of implant 10. According to one variation, two barbs 46 may be radially spaced about the perimeter of a wall section 44, however, in alternate embodiments more or less barbs may be provided as desired. In some embodiments, the geometry and spacing of the barbs may be varied between each wall or along an individual wall section 44. In general, barbs 46 may be configured and dimensioned to limit or reduce rotational, twisting, and/or lateral movement of implant 10 with respect to spinous processes when installed. In yet another embodiment, the wall sections 44 may have a star grind surface feature to limit rotational movement when installed. In other embodiments, one or more protrusions or spikes may be provided along central portion 24 and may extend radially outward to engage the spinous process.

In some embodiments, all or a portion of implant 10 may be resiliently compressible or expandable in the cranial-caudal direction such that the implant may support and or adjust to dynamic movement of the spine. For example, according to one embodiment, central support portion 24 may include a flexible bumper member to at least partially cushion the compression of adjacent spinous processes. In one variation, the bumper member may comprise a cylindrical sleeve provided to extend around the periphery of central support portion 24. In some embodiments, the bumper member may be integrated into the support portion and in alternate embodiments the bumper member may be fit over the support portion. In one variation, the bumper member may be made from biocompatible polyurethane, polycarbonate-urethane, elastomer, or other similar material. In still other embodiments, implant 10 may be made from varying materials along its length, such that for example the central support portion may be made from a resilient material, such as polyurethane, polycarbonate-urethane, elastomer or the like, and the end portions may be made from a rigid material, such as titanium or the like.

Figure 9:
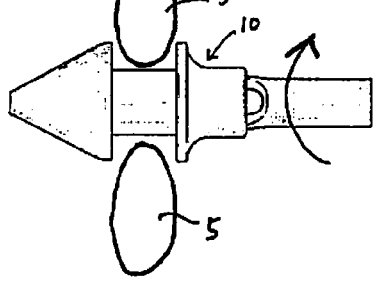
Figure 13:
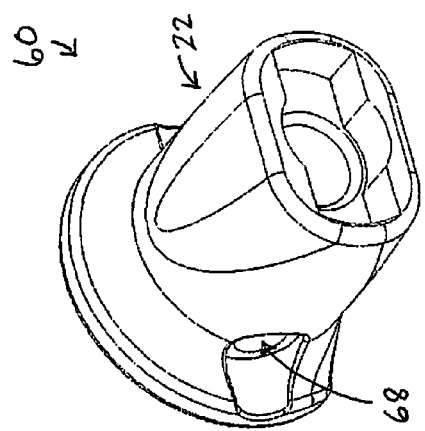
FIGS. 12-13 are front and rear perspective views of one embodiment a second end portion of the implant of FIGS. 10-11.
Figure 10:
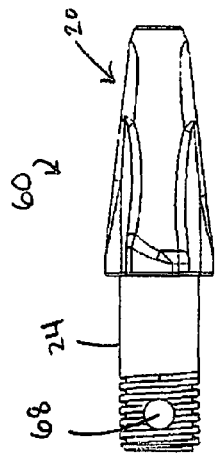
FIGS. 10-11 are side and perspective views of one embodiment a first end portion of another implant according to the invention.
Figure 11:
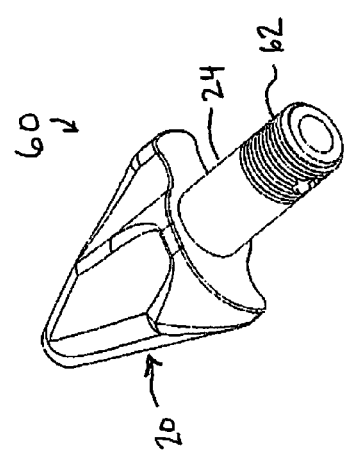
Figure 12:
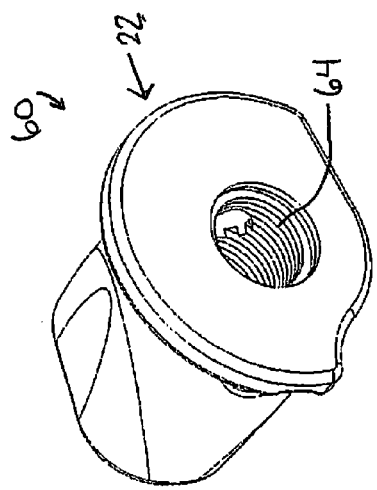

The implant itself may serve to dilate or distract the spinous processes as it is being inserted and/or after insertion. For example, in embodiments in which the implant is similar to that depicted in FIGS. 1-4, the first end 14 of implant 10 may be initially inserted or advanced laterally between compressed adjacent spinous processes as shown in FIGS. 5-9, for example. In one variation, the supraspinous ligament is not removed. In an initial pre-implantation condition, shown in FIG. 5, the adjacent spinous processes 5 may be compressed or narrowly spaced such that the initial space or longitudinal distance 50 between the processes may be about equal to or slightly larger or smaller than distance (b) of implant 10. During lateral insertion of the implant, one or more ramp surfaces or portions of the implant may contact one or both of the spinous processes 5 and may initially distract the processes a distance (b). As the implant is advanced laterally, the ramp 32 and/or the wedged or tapered shape of the distraction portion may distract the spinous processes further apart from one another, until the implant is advanced laterally into an implanted position (FIGS. 8-9) and the spinous processes are fitted into the central support portion 24 of the implant 10. In operation, the ramp surfaces engage the adjacent spinous processes as the implant is laterally advanced to act or perform in a cam-like manner to translate the lateral force to separate the spinous processes in the longitudinal or cranial-caudal direction as the implant is advanced. The maximum distraction of spinous processes by the implant 10 is distance (c) depicted in FIG. 7. According to one embodiment, distance (c) is greater than distance (a) such that the spinous processes 5 may be slightly "over distracted" during installation. In this regard, one skilled in that art may appreciate that such an over distraction may facilitate enhanced tactile feedback to a surgeon during installation as the spinous processes drop into the central support portion to signify a desired lateral placement in the patient with the spinous processes positioned within the central support portion. Once the implant is laterally advanced to the position shown in FIG. 8, the flange 39 of trailing end portion 22 may contact and/or abut the lateral side of the spinous processes to prevent further lateral translation and implant 10 may be subsequently rotated about one quarter turn or about 90 degrees into the final implantation position as shown in FIG. 9. In this regard, in the final implantation position, the shoulder wall sections 44 may contact the lateral sides of the spinous processes to limit or block movement of the implant along axis 12 and/or dislodgement from the interspinous space. Also, once the implant is implanted and after the spinous processes are fitted into the central support portion 24, the implant may maintain the spinous processes in a distracted or spaced condition, for example where the distance (a) of the implant is greater than a pre-implantation distance between the spinous processes.

Figure 14:
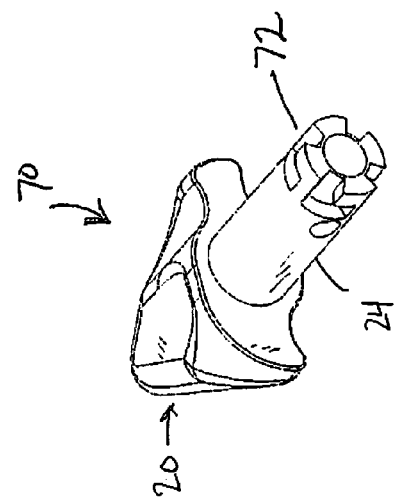
FIGS. 14-15 are side and perspective views of another embodiment a first end portion of another implant according to the invention.
Figure 15:
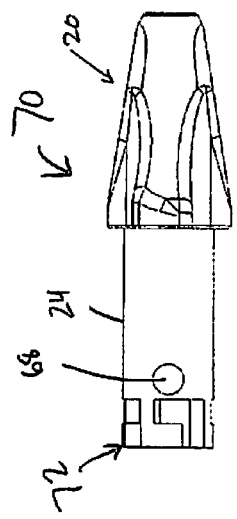
Figure 16:
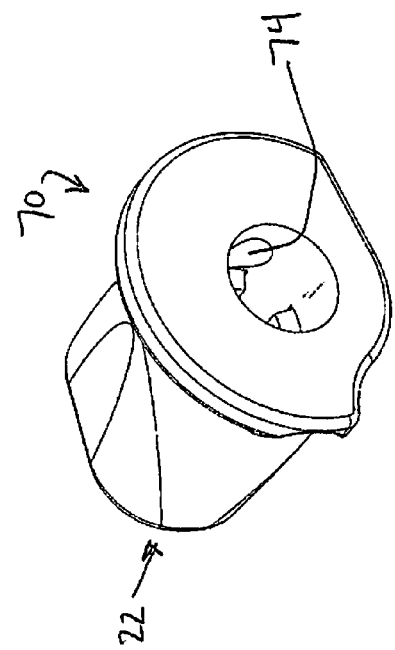
FIG. 16 is a front perspective view of another embodiment a second end portion of the implant of the implant of FIGS. 14-15.
Figure 18:
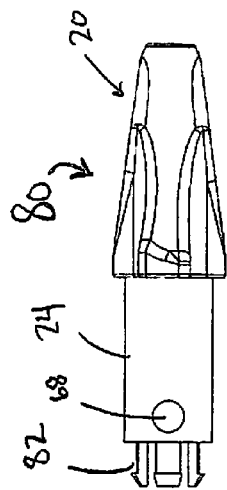
FIGS. 17-18 are side and perspective views of another embodiment a first end portion of another implant according to the invention.
Figure 19:
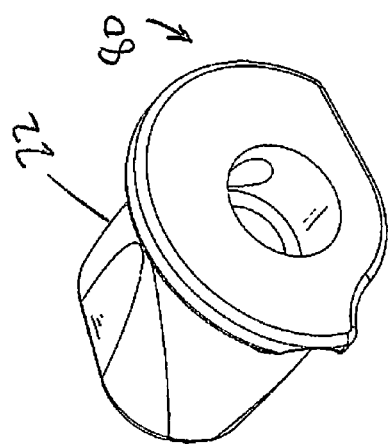
FIG. 19 is a front perspective view of another embodiment a second end portion of the implant of the implant of FIGS. 17-18.
Figure 17:
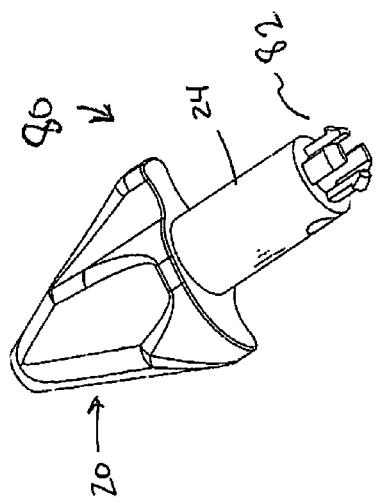

Referring now to FIGS. 10-19, various alternative embodiments of two-piece implant assemblies are shown with the trailing end 22 detachably connectable to the central support portion 24. In this regard, the implant assemblies may readily accommodate a flexible bumper member as described above. For example, in a variation wherein the bumper comprises a cylindrical sleeve, the sleeve may be assembled over the central support portion prior to attaching the trailing end portion 22 to the central support portion 24. Referring to FIGS. 10-13, one embodiment of an interspinous process implant assembly 60 is shown disassembled. Implant 60 is similar to implant 10 described above, however, in this embodiment implant 60 is an assembly of two pieces with the trailing end portion 22 threadably attachable to central support portion 24. In this embodiment, external threading 62 may be provided on the proximal end of support portion 24 which may engage internal threading 64 provided on trailing end portion 22. A pin, set screw or other fixation element 66 may extend at least partially through the trailing end portion 22 and through opening 68 in support portion 24 to fixedly secure the central support portion 24 to the trailing end portion 22. In this regard, fixation element 66 prevents undesirable disassembly of assembly 60. Referring to FIGS. 14-16, an alternative two-piece implant 70 is shown with a bayonet type connection between the trailing end 22 and central support portion 24. In this embodiment, bayonet type fingers 72 may be provided on the proximal end of support portion 24 which may engage internal bayonet feature 74 provided on trailing end portion 22 to connect the trailing end to the central support portion 24. Referring to FIGS. 17-19, an alternative two-piece implant 80 is shown with a snappable connection between the trailing end 22 and central support portion 24. In this embodiment, prongs 82 may be provided on the proximal end of support portion 24 which may engage internal indentations provided on trailing end portion 22 to connect the trailing end to the central support portion 24.

Figure 20:
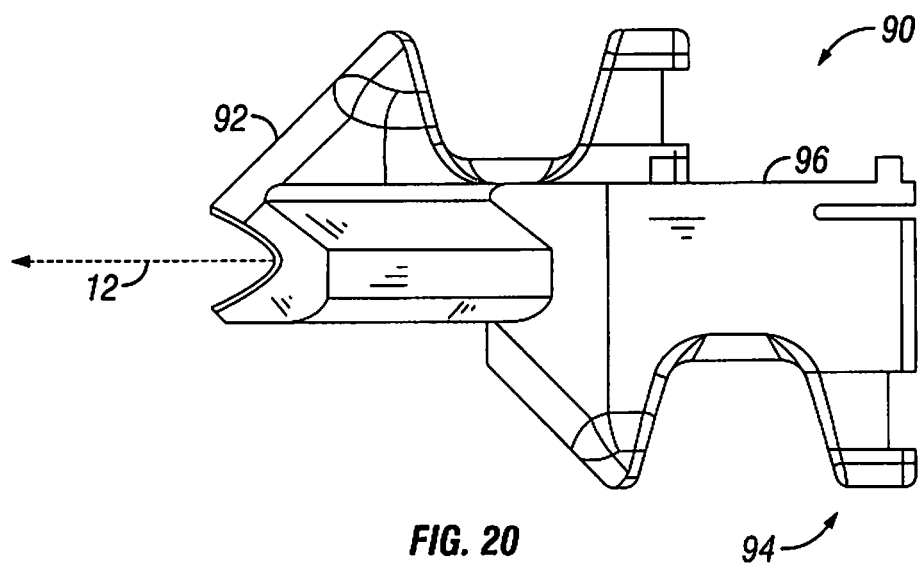
FIGS. 20-23 are side and perspective views of another embodiment of an implant according to the invention for creating, increasing, or maintaining distraction between adjacent spinous processes.
Figure 21:
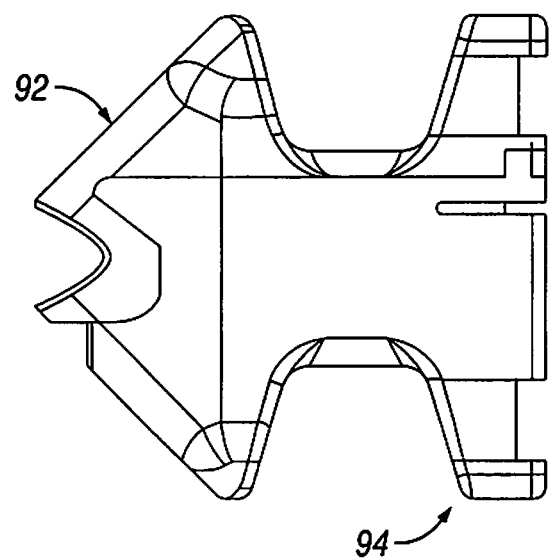
Figure 22:
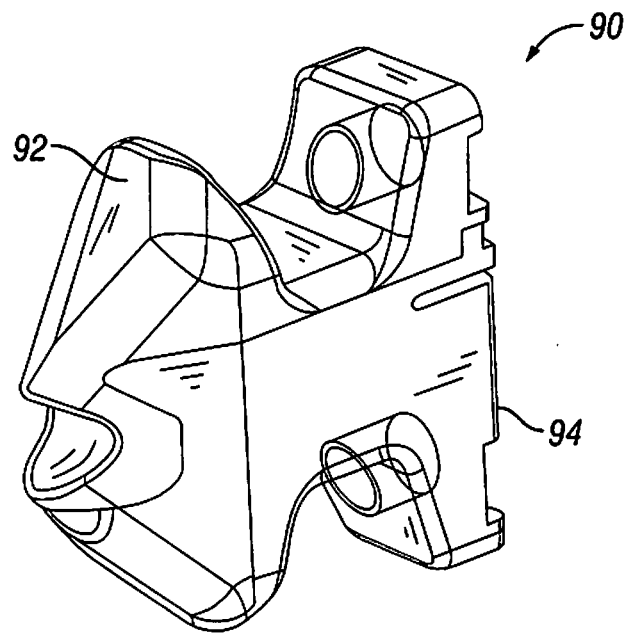
Figure 23:
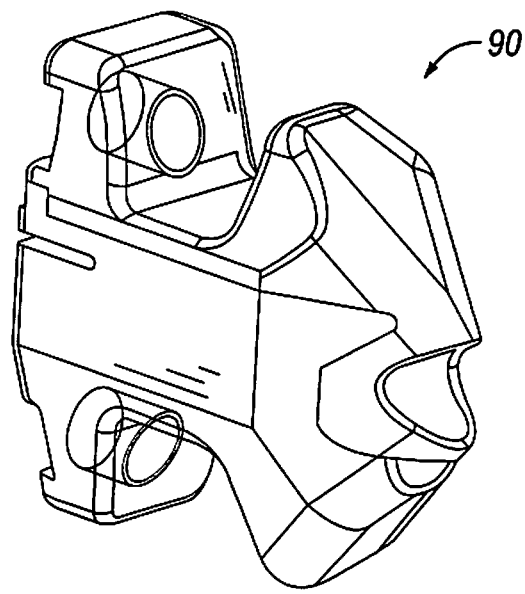

Referring now to FIGS. 20-23, another embodiment of a two-piece implant assembly 90 is shown with a first portion 92 slidably disposed about a second portion 94. According to this embodiment, first portion 92 and second portion 94 are slidable with respect to each other along axis 12 or along the length of the implant. According to one aspect of this embodiment, the first and second portions 92, 94 are interlockingly connected such as with a dovetail (or other interlocking shape) to allow one half of the implant to slide onto the other. Referring to FIG. 20, in an initial position first portion 92 may be disposed proximally along axis 12 and second portion 94 may be disposed distally. As shown in FIG. 21, second portion 21 may be slidingly advanced along axis 12 such as for example during implantation in the interspinous space. For example, the first portion 92 may be initially advanced into the interspinous space until the distraction portion 20 reaches the contralateral side of the spinous processes and the second portion 94 may subsequently be advanced into the interspinous space. In this regard, those skilled in the art may appreciate that implant 90 may cause less distraction of the interspinous space than an integral implant. A deflectable arm 96 may be provided on the first portion to snappably engage the second portion once the first portion has been slidingly advanced in the distal direction, as shown in FIGS. 22-23. In this regard, the two pieces 92, 94 of the implant interlock to form a solid implant when placed in the interspinous space. Also, as best seen in FIGS. 22-23, when portions 92, 94 are interlocked, implant 90 has a generally similar profile to implant 10 described above.

Kits having at least one implant such as those depicted in FIGS. 1-24, may include various sizes of implants having varying heights (a), widths (d), and overall lengths (e), for example having variations with incremental distances. In one embodiment, a system or kit may be provided that has implants having heights (a) between about 6 mm to about 22 mm. For example, in one variation implants having heights (a) of 8 mm, 10 mm, 12 mm, 14 mm, 16 mm, 18 mm, and 20 mm may be provided. In another variation, a system or kit may be provided that has implants having widths (d) between about 6 mm to about 18 mm. For example, in one variation implants having widths (d) of 8 mm, 12 mm, and 16 mm may be provided. In yet another variation, a system or kit may be provided that has implants having overall lengths (e) between about 20 mm and about 65 mm. For example, in one variation implants having overall lengths (e) of 25 mm and 60 mm may be provided.

Material

Implants in accordance with the present invention may be made of one or more materials suitable for implantation into the spine of a mammalian patient. Materials in accordance with the present invention may be biocompatible with a mammalian patient and/or may have one or more surface coatings or treatments that allow the spacers to be biocompatible. Materials in accordance with the present invention may include one or more materials having sufficient load capability and/or strength to maintain the desired spacing or distraction between spinous processes. Depending on the design employed, certain embodiments may have components or portions made of a material having certain flexibility, as desired for the particular application. Additionally, the materials of the present invention may be made of one or more materials that maintain their composition and shape for as long a time as possible without degrading or decomposing or changing shape, such that replacement of the implant is avoided.

Suitable materials for use in accordance with the present invention would be known to those skilled in the art. Non-limiting examples include one or more materials selected from medical grade metals, such as titanium or stainless steel, biocompatible polymers, such as polyetheretherketone (PEEK), ceramics, deformable materials, bone, allograft, demineralized or partially demineralized bone, allograft ligament, polyurethane, and polycarbonate-urethane (for example, for portions of the insert where cushioning is desired). Similarly, any fastening devices may be made of materials having one or more of the properties set forth with respect to the implant itself. For example, screws or pins may include titanium and straps may include polyethylene. In some embodiments, primarily radiolucent material may be used. In this regard, radio-opaque material or markers may be used in combination with the radiolucent material to facilitate implantation. Exemplary radio-opaque material includes but is not limited to titanium alloys, tantalum or other known radio-opaque marker material. As indicated above, implants in accordance with the present invention may have one or more portions that may have modified surfaces, surface coatings, and/or attachments to the surface, which may assist in maintaining the spacer in a desired position, for example by friction. Other embodiments of implants according to the invention may include hydrophilic and/or hydrophobic coatings or combinations thereof. For example, all or part of an implant, such as all or part of distraction portion 20, may have a hydrophilic coating to reduce friction and facilitate lateral insertion between bony parts. Similarly all or part of an implant, such as all or part of central support portion 24, may have a hydrophobic coating to increase friction to deter dislodgement from between bony parts. Suitable surface modifications, coatings, and attachment materials would be known to those skilled in the art, taking into consideration the purpose for such modification, coating, and/or attachment.

Methods for Treating Stenosis and Methods of Inserting an Implant

Methods are provided for treating spinal stenosis. Methods are also provided for inserting an implant. These methods may include implanting a device to create, increase, or maintain a desired amount of distraction, space, or distance between adjacent first and second spinous processes. The adjacent first and second spinal processes may be accessed by various methods known by practitioners skilled in the art, for example, by accessing the spinous processes from at least one lateral side/unilateral, bilateral, or midline posterior approach.

Certain methods of the present invention include creating an incision in a patient to be treated, dilating any interspinous ligaments in a position in which the implant is to be placed in the patient, sizing the space between adjacent spinous processes (for example using trials), and inserting an implant of the appropriate size between the adjacent spinous processes. Methods of the present invention may include securing the implant to one or more of the spinous processes, to one or more other portions of the patient's spine, and/or to itself such that the implant maintains its position between the spinous processes.

Methods of the present invention may include dilating or distracting the spinous processes apart from one another before sizing and/or before inserting the implant. Methods may vary depending on which implant is being inserted into a patient. For example, certain implants may require distracting the spinous processes apart before inserting the implant, while other implants may themselves dilate or distract the spinous processes while inserting the implant. In embodiments where the implants themselves dilate or distract the spinous process, the implant may have, for example, a predetermined shape to dilate, distract, or otherwise move or separate apart adjacent spinous processes such as a cam or cam-like profile, it may have a distraction device that is deployed, and/or it may have a tapered expander to distract an opening between the adjacent spinous processes or other features to facilitate distraction of the adjacent spinous processes.

According to certain embodiments, spacers may be placed between the spinous processes anterior to the supraspinous ligament, avoiding the nerves in the spinal canal. The procedure may be performed under local anesthesia. For surgical procedures, in which an implant is being inserted into the lumbar region, the patient may be placed in the right lateral decubitus position with the lumbar spine flexed or in another flexed position. According to one method, a surgeon may desire to use fluoroscopy to align in parallel the adjacent vertebral bodies corresponding to the adjacent spinous processes to gauge the desired distraction distance.

According to certain embodiments, one or more probes may be used to locate the space between the spinous processes. Depending on the design of the spacer to be inserted, the space may be widened, for example with a dilator before inserting the implant.

Figure 24:
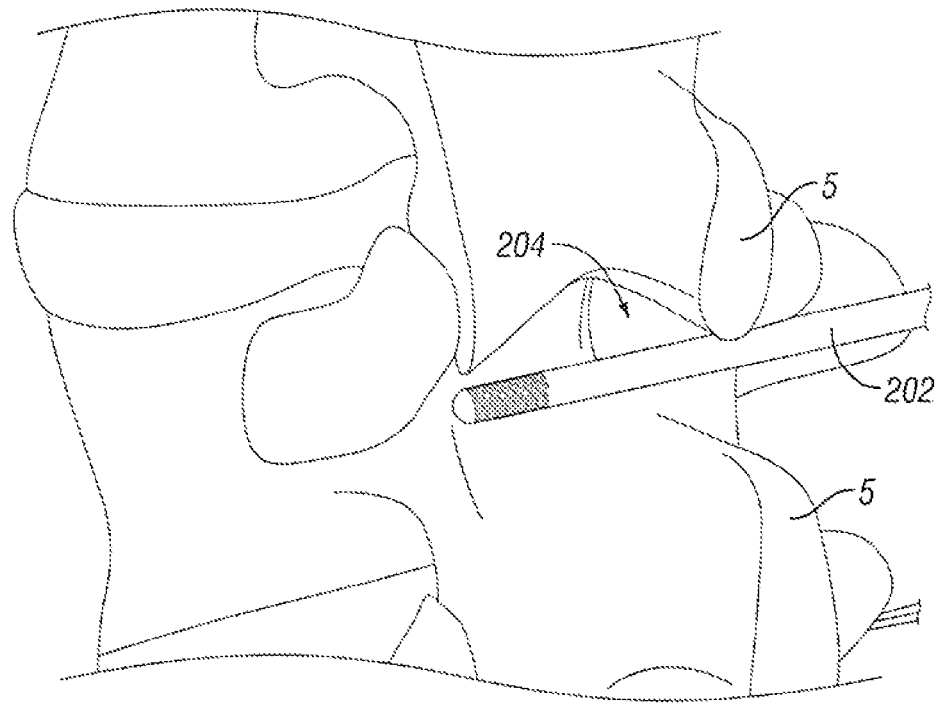
FIGS. 24-32 are perspective views demonstrating various steps according to one embodiment of a method of installation of the implant of FIG. 1.
Figure 25:
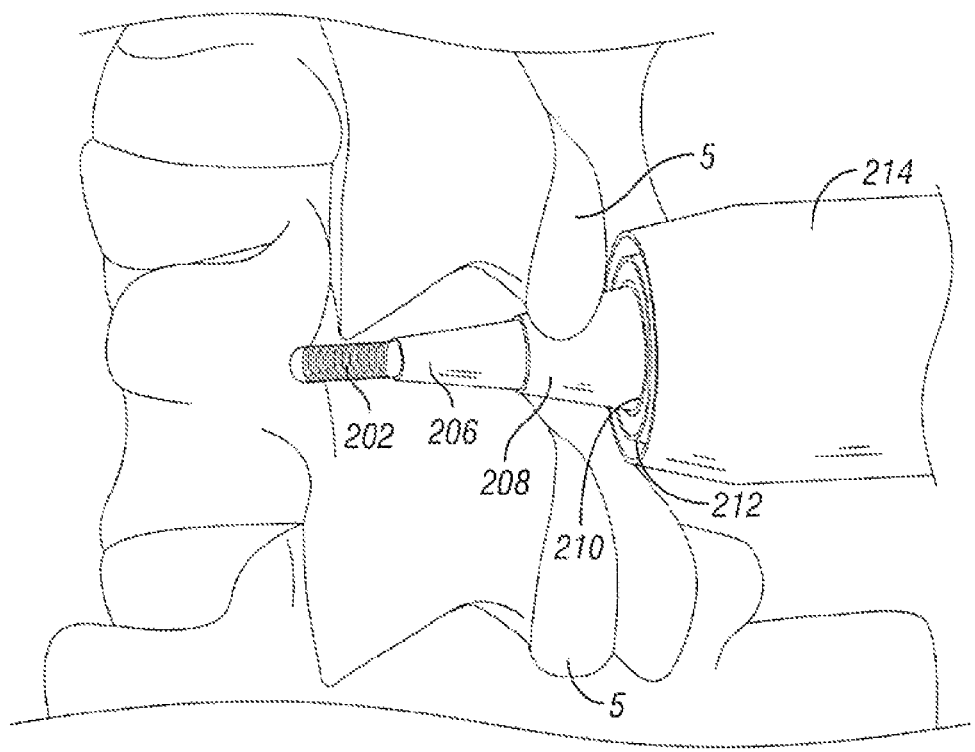
Figure 26:
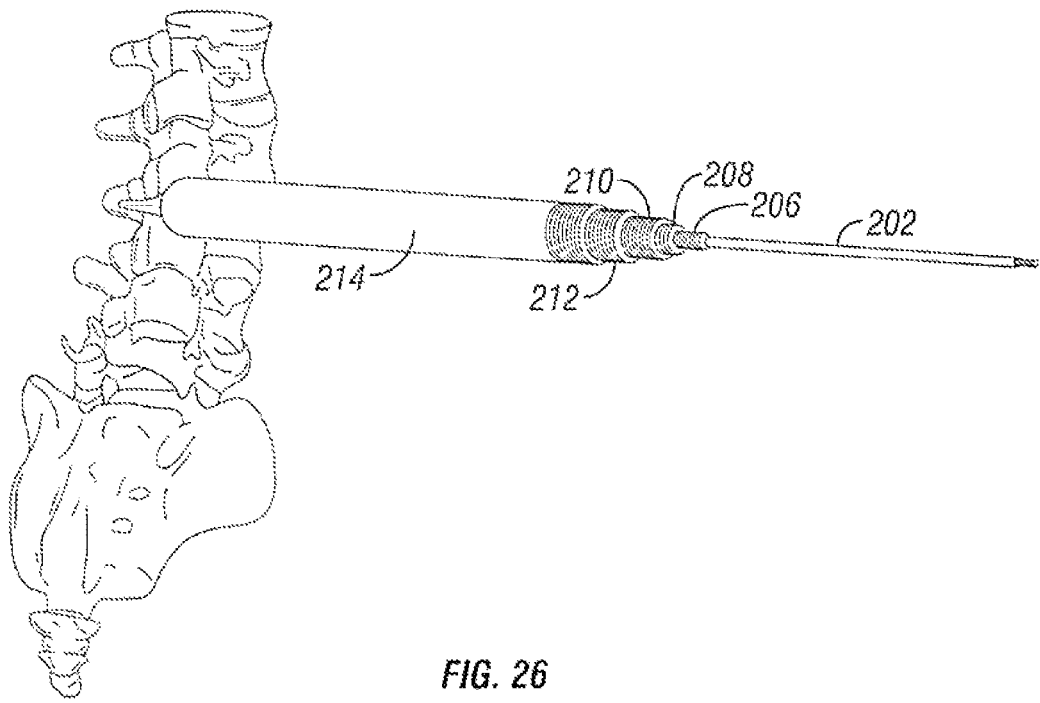
Figure 27:
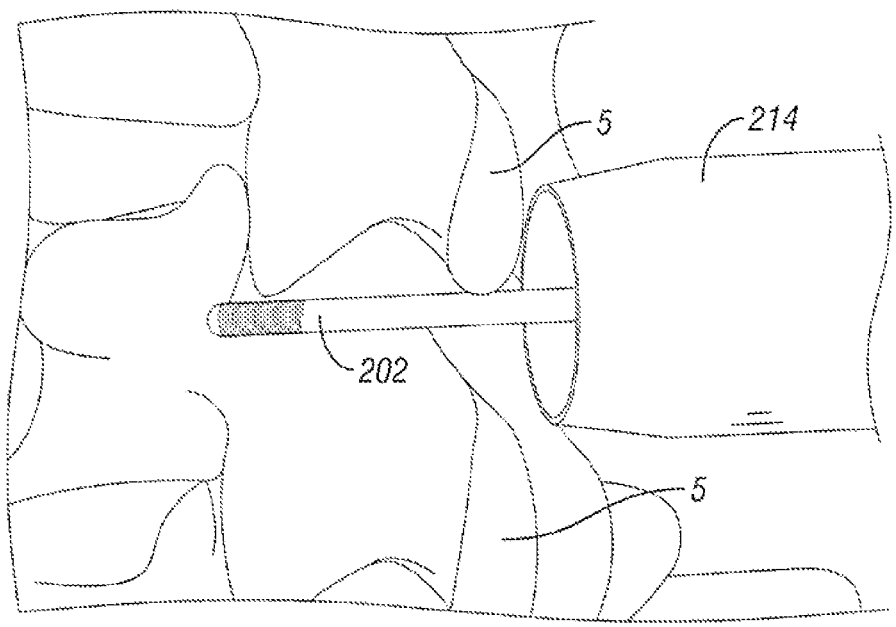
Figure 28:
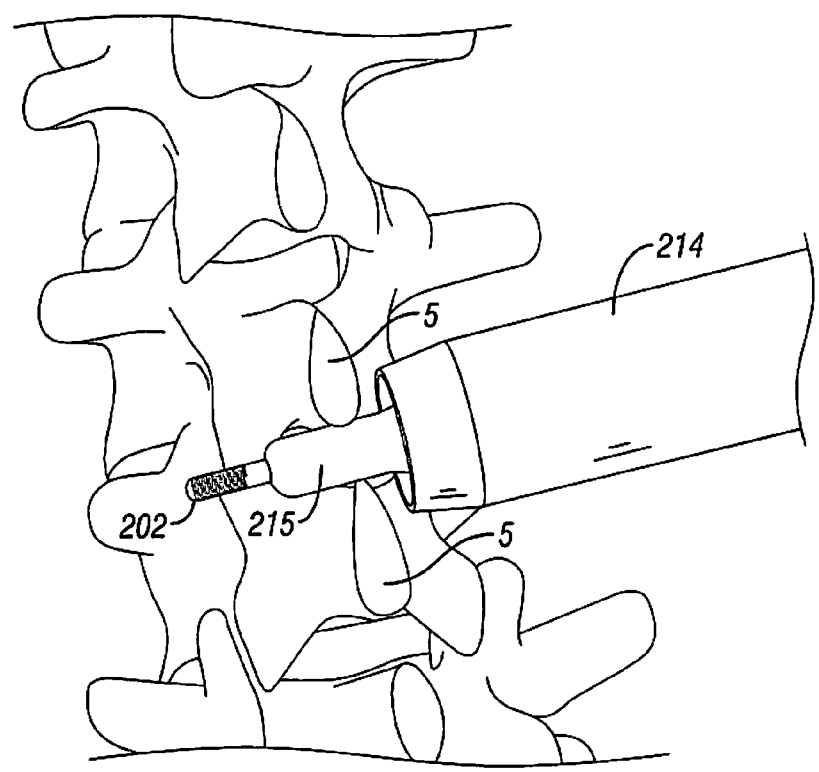
Figure 29:
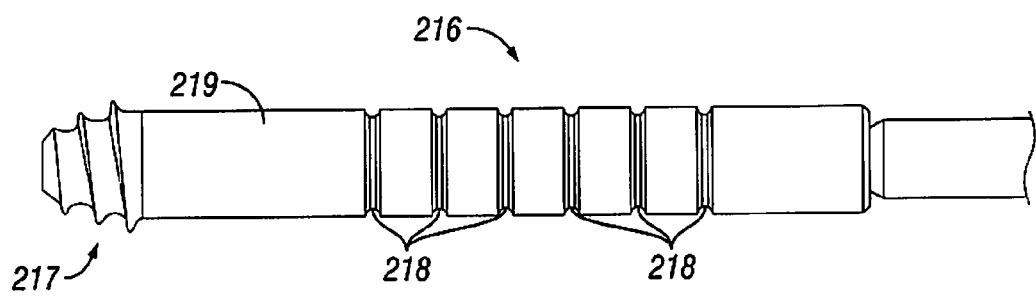

Referring to FIGS. 24-32, one embodiment of a surgical method according to the invention for implanting an implant 10 in the spine is disclosed. According to this embodiment, the adjacent first and second spinal processes 5 may be accessed from one lateral side through a minimally invasive procedure. In this regard, according to certain methods of the invention, a unilateral approach may be used to install implant 10 without removal of the supraspinous ligament. In this method, as shown in FIG. 24, a guide wire 202, such as a K wire, is inserted laterally through the skin and into the interspinous space 204. According to one method, a working portal may be created concentric to the guidewire 202, as shown in FIGS. 25-26, by inserting a series of sequentially larger diameter tubes 206, 208, 210, 212, 214 to dilate the tissue surrounding guidewire 202. Referring to FIG. 27, once a dilating tube having a sufficiently large inner diameter to accommodate implant 10 is positioned about guidewire 202, the smaller diameter tubes 206, 208, 210, 212 may be withdrawn, leaving the guidewire 202 and the outer tube 214. Referring to FIG. 28, one or more trials 215 may then be inserted to appropriately size the interspinous space 204 and the trials 215 may also be utilized to dilate interspinous ligaments. In one exemplary embodiment, a generally cannulated cylindrical trial 215, shown in FIG. 28, may be utilized to size the space between adjacent processes 5. Referring to FIG. 29, an alternate embodiment of a trial 216 that may be used is shown which may comprise a ramped tip portion 217 adjacent its distal end and multiple longitudinal indentations or markings 218 on at least a portion of central portion 219 and may provide visual indication when viewed under fluoroscopy of the width of the spinous processes and facilitate the surgeon's selection of an appropriately sized implant. Similarly, the appropriate diameter of central portion 219 of trial 216 may be selected to gauge the amount of distraction desired. In this regard, the spacing of the spinous processes may be viewed under fluoroscopy to facilitate the surgeon's selection of an appropriately sized implant. Finally, an implant of the appropriate size may be inserted between the adjacent spinous processes.

Figure 30:
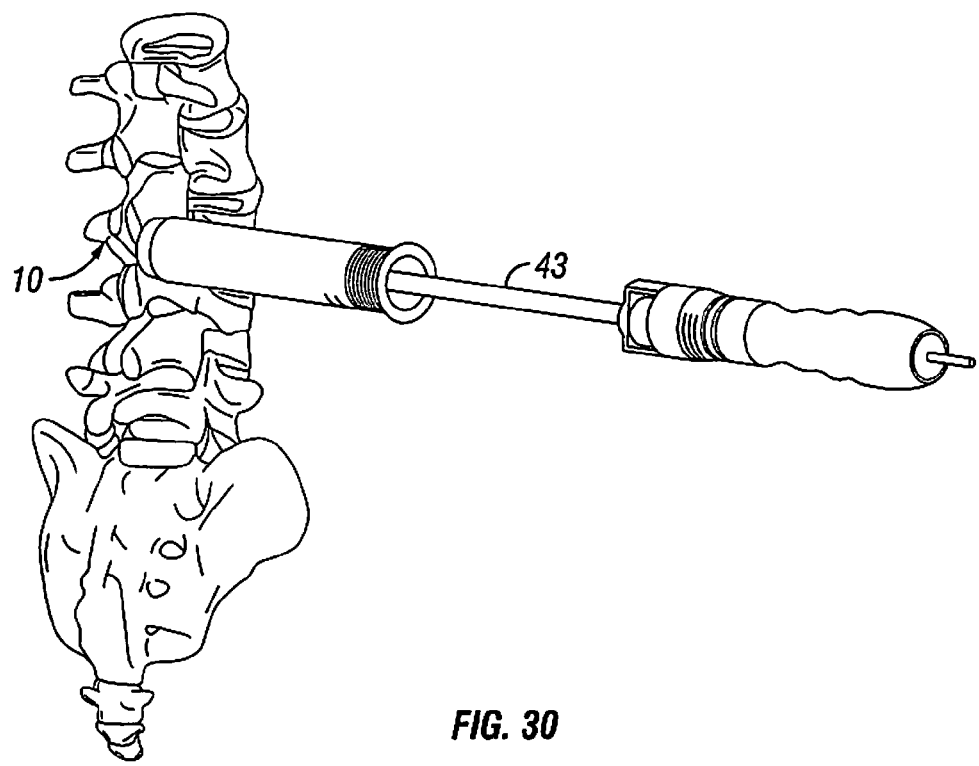
Figure 31:
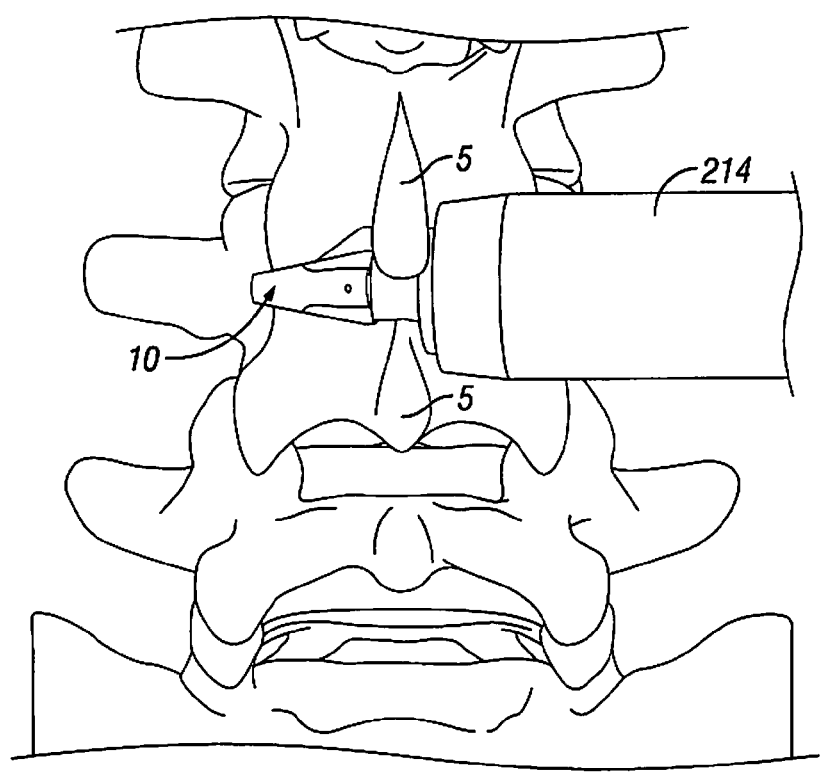
Figure 32:
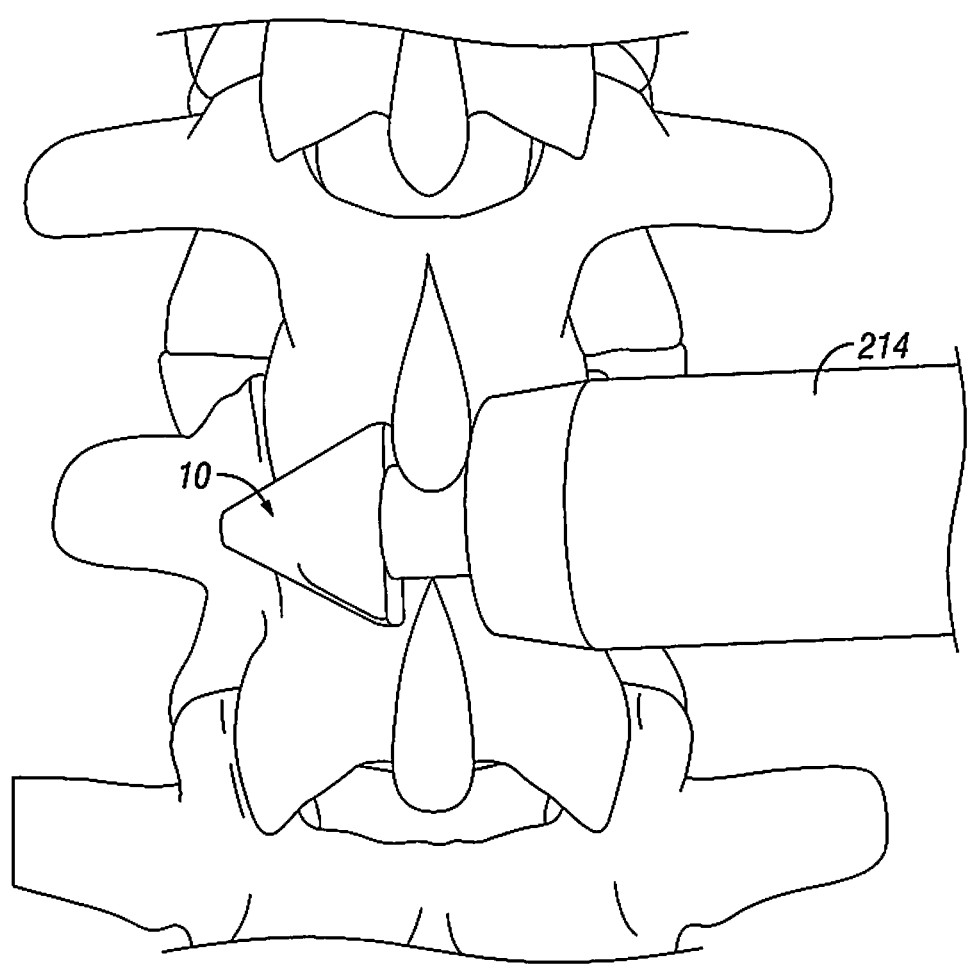
Figure 34:
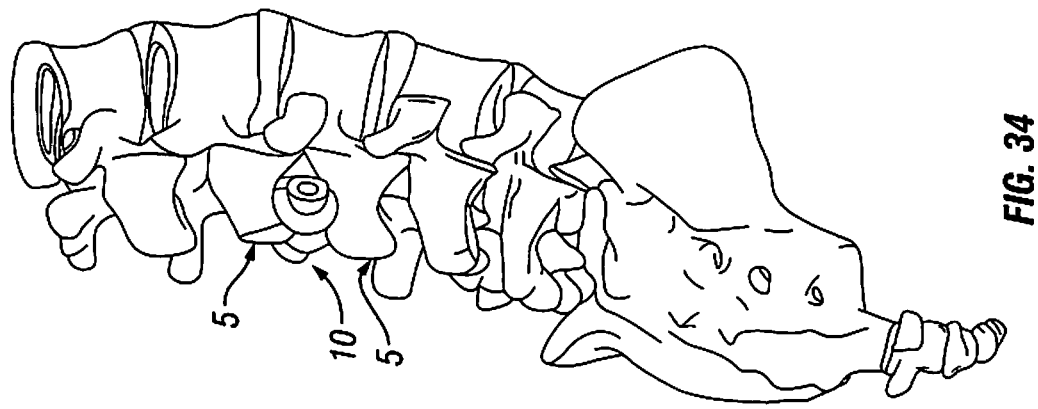
FIGS. 33-34 depict perspective views of the implant of FIG. 1 shown in an implanted position.
Figure 33:
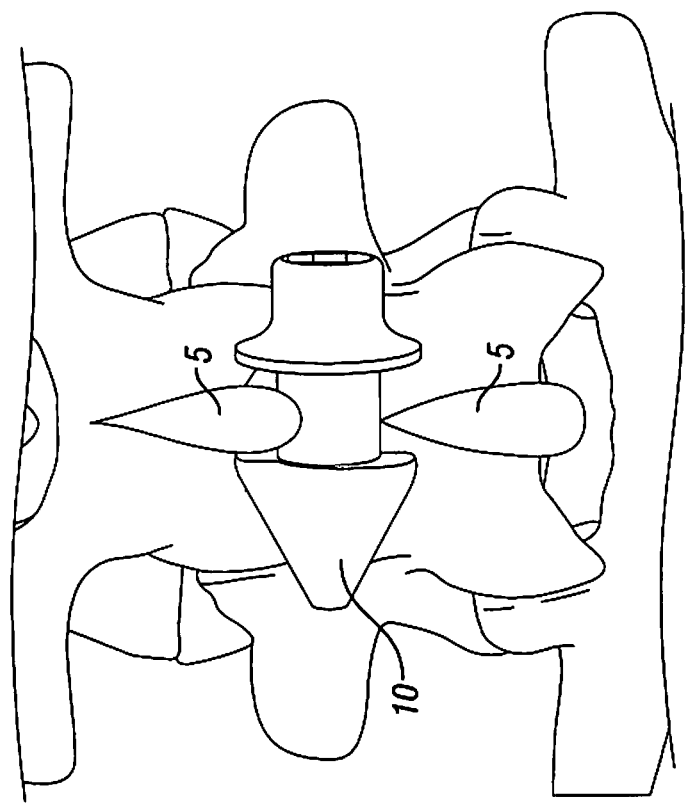
Figure 35:
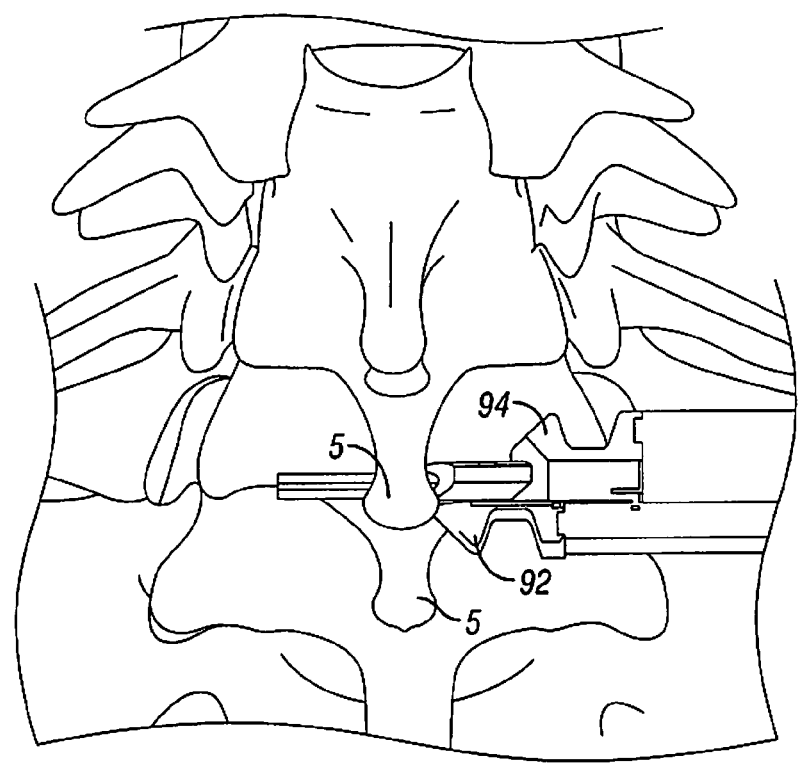
FIGS. 35-38 are perspective views demonstrating various steps according to one embodiment of a method of installation of the implant of FIGS. 20-23.

Referring to FIGS. 30-32, one exemplary embodiment of a method of installing implant 10 is shown. Implant 10 is advanced laterally over guidewire 202 through cannulation 18 to the interspinous space 204. During lateral insertion of the implant between the spinous processes, one or more ramp surfaces or portions of the implant may contact one or both of the spinous processes 5 and may initially distract the processes. Implant 10 may be laterally advanced along the guidewire to further advance implant 10 between the spinous processes and, the wedged or tapered shape of the distraction portion 20 may distract the spinous processes further apart from one another, until the implant is in an implanted position (FIGS. 31-34) with the distraction portion 20 positioned on the contralateral side of the spinous processes and the spinous processes are fitted into the central support portion 24 of the implant 10. Once the implant is laterally advanced to the position shown in FIG. 31, the flange 39 of trailing end portion 22 may contact and/or abut the lateral side of the spinous processes to prevent further lateral translation and implant 10 may be subsequently rotated about one quarter turn or about 90 degrees into the final implantation position as shown in FIG. 32. In this regard, in the final implantation position, the shoulder wall sections 44 may contact the lateral sides of the spinous processes to limit or block movement of the implant along axis 12 and/or dislodgement from the interspinous space. Referring to FIGS. 33-34, once implant 10 is installed, the guidewire may be removed through the cannulation leaving the implant 10 in the interspinous space.

Figure 36:
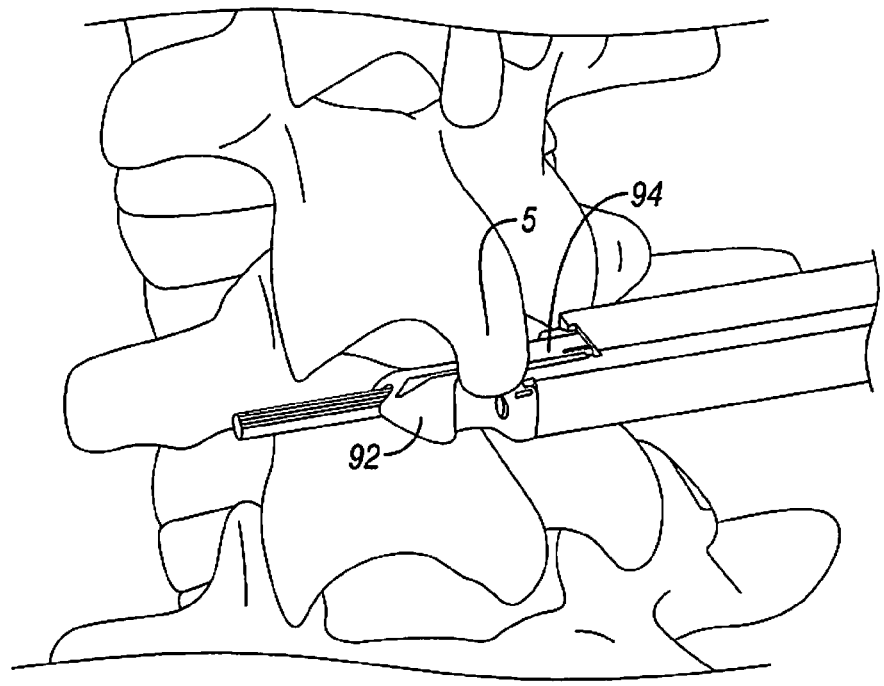
Figure 37:
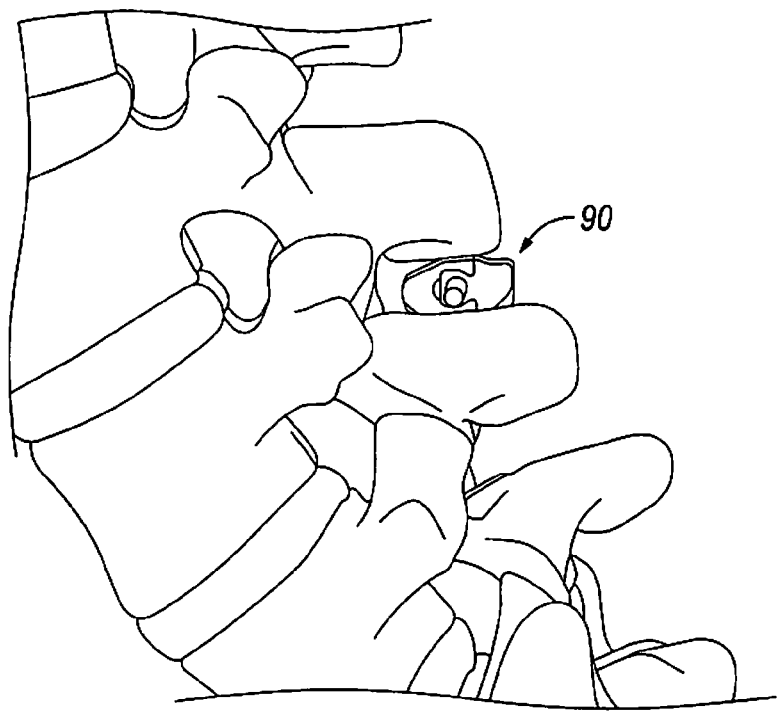
Figure 38:
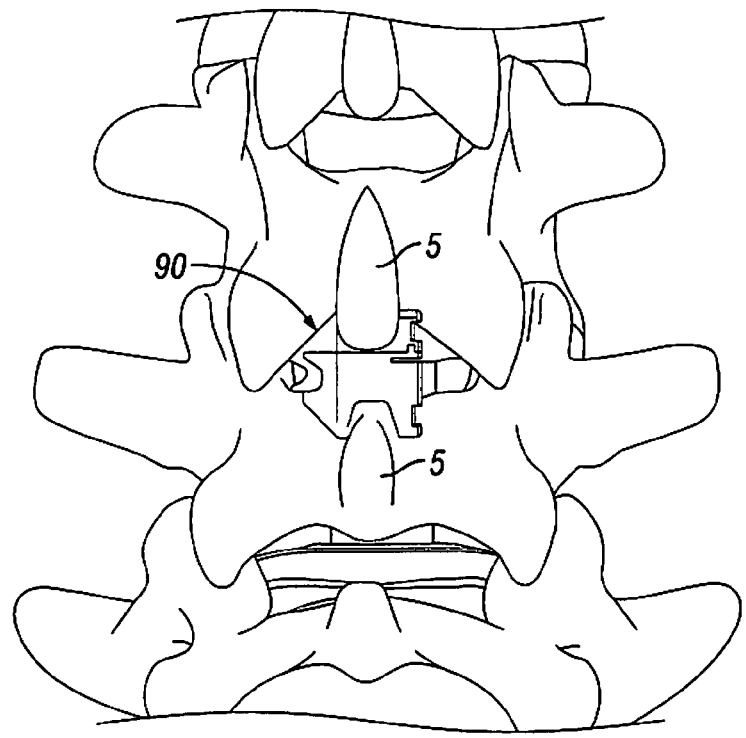

Referring to FIGS. 36-41, one exemplary embodiment of a method of installing implant 90 is shown. Implant 90 is advanced laterally over guidewire 202 through cannulation 18 to the interspinous space 204. Referring to FIGS. 36-37 the first portion 92 may be initially advanced into the interspinous space until the distraction portion 20 reaches the contralateral side of the spinous processes. As shown in FIGS. 38-40, the second portion 94 may subsequently be advanced into the interspinous space. Once the implant is laterally advanced to the position shown in FIG. 40, implant 90 may be subsequently rotated about one quarter turn or about 90 degrees into the final implantation position as shown in FIG. 41. Referring to FIG. 41, once implant 90 is installed, the guidewire may be removed through the cannulation leaving the implant 10 in the interspinous space.

While the invention herein disclosed has been described by means of specific embodiments and applications thereof, numerous modifications and variations can be made thereto by those skilled in the art without departing from the scope of the invention.

We claim:
1. A method for stabilizing the vertebral column comprising:
   accessing an area between adjacent spinous processes;
   positioning an implant between adjacent spinous processes, the implant comprising:
      a cannulated body comprising a support portion extending laterally along a lateral axis between first and second end portions, the body defining a cannula extending therethrough along the lateral axis;
      wherein at least a portion of the first end portion extends beyond the support portion in a direction perpendicular to the lateral axis;
      wherein the device is configured and dimensioned to be inserted between adjacent spinous processes of the vertebral column in a lateral direction along the lateral axis and is advanceable over a guidewire extending through the cannula;
      wherein the first end portion is configured and dimensioned to engage and separate the adjacent spinous processes when inserted and to advance the device in the lateral direction to position the support portion in a predetermined position between the spinous processes;
      wherein the first end portion comprises a generally wedge shape, the wedge shape defining a first cone angle in the lateral direction angled towards a tip of the first end portion and a second cone angle in a vertical direction, angled towards the tip of the first end portion, that is perpendicular or transverse to the lateral axis; and
      wherein the first cone angle is greater than the second cone angle; and
   rotating the implant from a first configuration to a second configuration relative to the spinous processes, wherein in the first configuration the second end portion has a first height and in the second configuration the second end portion has a second height that is greater than the first height.

2. The method of claim 1, wherein at least a portion of the second end portion extends beyond the support portion in a direction perpendicular to the lateral axis.

3. The method of claim 1, wherein the body is made from a polyetheretherketone (PEEK) material.

4. The method of claim 1, wherein the first end portion comprises a generally frustoconical shape.

5. The method of claim 1, wherein the first end portion comprises a ramp, wherein the ramp is linearly shaped.

6. The method of claim 1, wherein the support portion is configured and dimensioned to fit between adjacent spinous processes and further comprises:
   a proximal support surface spaced longitudinally from a distal support surface by a first distance, the support surfaces configured to contact adjacent spinous processes of the vertebral column, wherein the first distance is predetermined for spacing of two adjacent spinous processes when the device is implanted in the vertebral column.

7. The method of claim 1, wherein the support portion has a generally circular cross-section.

8. The method of claim 1, wherein the body is made from a titanium material.

9. The method of claim 2, wherein a portion of the end portions are configured and dimensioned to contact the lateral sides of the spinous process when the device is implanted in the vertebral column.

10. The method of claim 1, wherein the body is configured and dimensioned to be rotated in-situ to position the first and second end portions on opposite lateral sides of the spinous processes.

11. The method of claim 1, wherein the body is maintained in an implanted position without additional fixation devices.

12. A method for implantation in a treated area of an intervertebral space between vertebral bodies of a spine, comprising:
   accessing the treated area of the intervertebral space between vertebral bodies;
   positioning an implant in the treated area, the implant comprising:
      a spacer body comprising a central support portion extending along a lateral axis between first and second end portions,
      the central support portion comprising a superior support surface and an inferior support surface, wherein the superior and inferior support surfaces each have a contact area capable of engaging with anatomy in the treated area and the superior and inferior surfaces are spaced apart a first distraction distance,
      the first end portion comprising a generally wedge shape, the wedge shape having a superior end surface and an inferior end surface, the superior and inferior end surfaces each have a contact area capable of engaging with anatomy in the treated area and the first and second surfaces are spaced apart a second distraction distance, the wedge shape further defining a first cone angle in a lateral direction along the lateral axis angled towards a tip of the first end portion and the wedge shape further defining a second cone angle in a vertical direction, angled towards the tip of the first end portion, that is perpendicular or transverse to the lateral axis, wherein the first cone angle is greater than the second cone angle,
      wherein the first distraction distance is less than the second distraction distance,
      wherein when the device is in a first implantation position the adjacent vertebral bodies are maintained substantially separated by at least the second distraction distance and when the device is in a second implantation position the adjacent vertebral bodies are maintained substantially separated by at least the first distraction distance, and
      wherein the spacer body support portion is laterally advanceable from the first implantation position to the second implantation position; and
   rotating the implant from a first configuration to a second configuration relative to the spinous processes, wherein in the first configuration the second end portion has a first height and in the second configuration the second end portion has a second height that is greater than the first height.

13. The method of claim 12, wherein the first end portion is tapered along its longitudinal length.

14. The method of claim 12, wherein the body defines a cannula extending along the lateral axis through the body, the cannula configured and dimensioned for receiving a guidewire therethrough such that the device is advanceable over the guidewire.

15. The method of claim 12, wherein in the second implantation position the first and second end portions are located laterally adjacent opposite lateral sides of a portion of the vertebral bodies.

16. The method of claim 12, wherein the spacer body is maintained in the second implantation position without additional fixation devices.

17. The method of claim 12, wherein the first end portion comprises an outer surface and, the first end portion further comprising a ramp portion along the outer surface.

* * * * *